United States Patent [19]
Jacobs

[11] Patent Number: 4,653,633
[45] Date of Patent: Mar. 31, 1987

[54] ELECTRICAL CONDUCTOR

[75] Inventor: Howard L. Jacobs, Broadview Heights, Ohio

[73] Assignee: The B.F. Goodrich Company, New York, N.Y.

[21] Appl. No.: 636,635

[22] Filed: Aug. 1, 1984

Related U.S. Application Data

[63] Continuation-in-part of Ser. No. 331,709, Dec. 17, 1987, abandoned.

[51] Int. Cl.$^4$ ............................................. B65G 43/06
[52] U.S. Cl. .................................... 198/810; 198/856
[58] Field of Search ............. 198/502, 810, 856, 957, 198/502.1; 252/511; 340/675, 676; 423/447.1

[56] References Cited

U.S. PATENT DOCUMENTS

| | | | |
|---|---|---|---|
| 3,792,459 | 2/1974 | Snyder | 198/502 X |
| 4,296,855 | 10/1981 | Blalock | 198/502 |
| 4,382,024 | 5/1983 | Seaman et al. | 252/511 |

*Primary Examiner*—Robert J. Spar
*Assistant Examiner*—Lyle Kim
*Attorney, Agent, or Firm*—Woodrow W. Ban

[57] ABSTRACT

A conveyor belt having electrically conductive antennae spaced along the direction of movement of the belt and extending from edge to edge of the belt for carrying signals thereacross to detect rips in the belt. The antennae are constructed of a material, the major component thereof being a blend of natural and synthetic rubbers and also including 10% to 30% by weight of substantially electrically conductive carbon black to carry the signals thereacross.

5 Claims, 4 Drawing Figures

ELECTRICAL CONDUCTOR

This is a continuation-in-part of application Ser. No. 331,709, filed Dec. 17, 1981, now abandoned.

BACKGROUND OF THE INVENTION

In long endless conveyor belts of the type having a body formed from an electrically insulating material, used to convey bulk material, there is a possibility of encountering a rip in the belt. Rips may occur, for example by sharp objects being dropped upon the belt at a loading station. It is desirable to promptly detect particularly longitudinal rips and, preferably, to shut down and repair the conveyor belt upon such detection, thereby reducing the possibility for damage to the belt.

In prior structures as described, for example, in U.S. Pat. No. 3,792,459 a conveyor belt rip detection system is disclosed of a type having a plurality of spaced antennae imbedded transversely at spaced-apart locations in the belt to periodically couple an electrical signal from a transmitter probe to a receiver probe while the belt, with its respective antennae, moves past the probes. The detected electrical signals function to monitor the integrity of the belt and to shut down the conveying system in response to a break in an antenna which would be typically indicative of a longitudinal rip in the belt. Detection of the antenna break permits belt repair or replacement before the break or rip elongates and destroys an extended portion or even the entirety of the belt or before the conveyor belt assembly ceases to function properly as a consequence of the rip. A rip, noted timely, can be corrected with relatively minimal cost and inconvenience.

In prior devices it has been the general practice to utilize antennae made of metallic screens or wires such as steel wires, extending transversely across the width of the belt, at spaced apart distances. Such screen or wire antennae function properly during normal operations for a period of time.

Frequently, however, due to movement of the belt and wires around conveyor rollers in the conveyor system, continued flexing stresses upon the screen or wires of the antennae may cause premature breakage of the wires, thus causing a malfunction in the rip detection system. Metallic wires are also susceptible to breakage caused by ore dropped on the belt at a loading station. A broken antenna, caused by a failure of any nature, undesirably will give the appearance to a conveyor belt control system that a rip exists in the belt. The control system could then improperly shut down the conveying system when in fact no such rip exists in the belt. Alternate decisional programming of the control system may also be employed.

Priorly, as described in U.S. Pat. No. 4,296,855 issued to Gary L. Blalock, antennae have been constructed of a knit or woven, carbon infused non-metallic fiber such as nylon. Such antennae have performed satisfactorily having mechanical properties superior to metallic screen type antennae.

SUMMARY OF THE INVENTION

The present invention provides an improved electrical conductor particularly useful as an antenna for utilization in conveyor belt rip detecting systems.

In accordance with a preferred embodiment of the instant invention, each antenna is constructed principally of natural and synthetic rubber, blended with a significant portion of carbon black having a substantial electrical conductivity and with the remaining minority of components being wear resisting agents, antioxidants, vulcanization promoters and other additives generally extending the life of the antennae and improving their mechanical, chemical and electrical properties. When vulcanized into a conveyor belt at spaced apart points along the belt length, such rubber antennae members can function as antennae for rip detection purposes.

A rip detecting system provided with a belt having conductive rubber antennae integrally vulcanized into the belt enjoys a reduction in premature breakage of the antennae since the conductive rubber antennae can undergo elongation more effectively than prior antennae without significant loss of substantial electrically conductive properties. Employing antennae of the instant invention assures great impact resistance for belts in which they are employed. Improved control system performance results since premature breakage of belt antennae would cause the loss of electrical conductivity across the belt between the probes in a control system of the type disclosed in the aforementioned patent to Snyder. The new antennae are also generally less expensive than prior antennae devices and easier to fabricate into belt systems. Being vulcanized into the belt, the antennae of this invention exhibit improved mechanical integrity since the antennae are part of the belt composite, effectively being bonded as one with the belt.

In order to gain a better understanding of the invention as well as other advantages and further features thereof, reference is made to the following detailed description of the invention to be read in conjunction with the accompanying drawings together forming part of the specification.

DESCRIPTION OF THE PREFERRED EMBODIMENT

Figure 1:
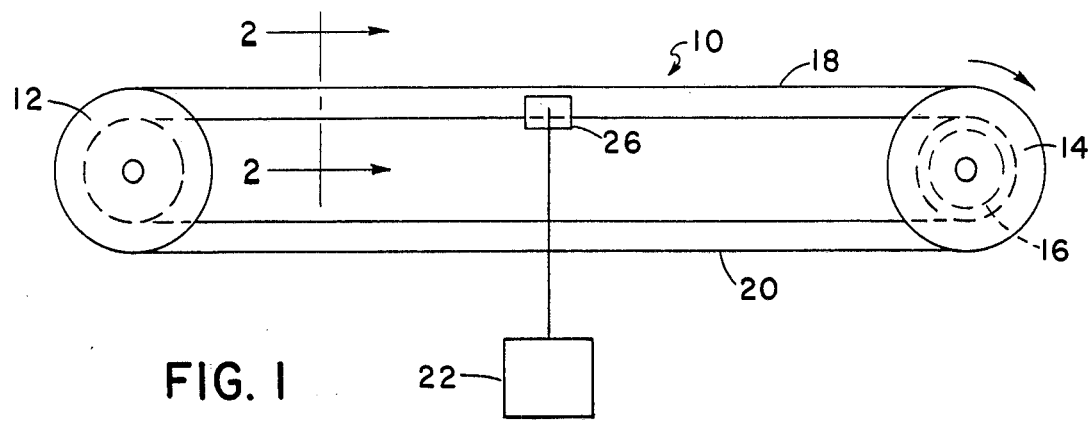
FIG. 1 is a schematic side elevational view of a conveyor assembly and control system adapted to utilize antennae constructed in accordance with the instant invention.
Figure 2:
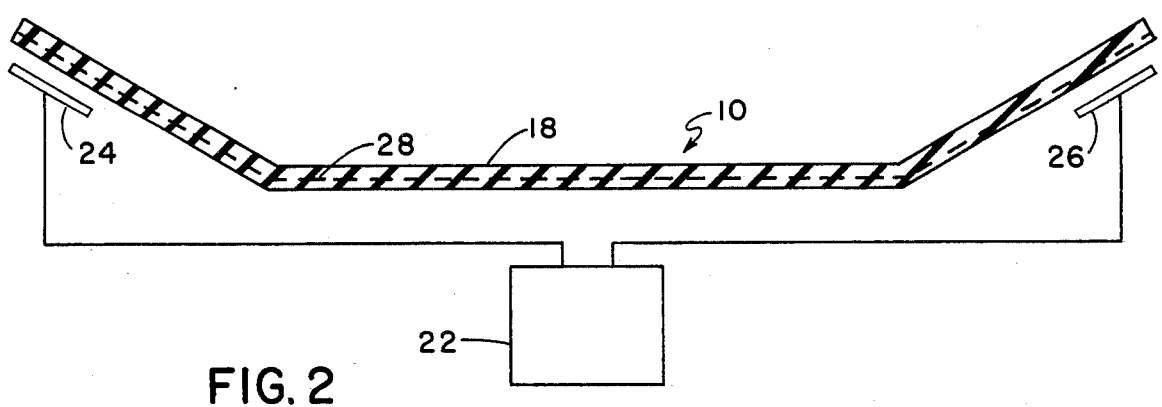
FIG. 2 is a schematic sectional view of the assembly of FIG. 1 taken through the belt, antenna, sensor probes, and control circuitry.

Referring to the drawings, FIG. 1 depicts an endless conveyor belt assembly constructed to utilize an antenna made in accordance with the instant invention. The conveyor belt, generally designated as 10, is trained around a plurality of rollers 12 and 14 powered by a drive means such as a motor 16, to move the belt in a continuous cycle of operation. The conveyor belt assembly includes an upper zone or track 18 for conveying ore or other material between a loading station and a discharge station. Opposite the upper zone is a belt return zone 20. The edges of the belt are preferably turned up slightly at least along the upper zone 18 to minimize spillage of conveyed ore therefrom.

The belt 10 is schematically shown as traveling over a short distance between two rollers, 12, 14. It should be understood that belts 10 of this type are readily adapted for conveying ore over great distances including many hundreds or thousands of yards. While only two rollers, 12 and 14, are shown for illustrative purposes, many roller configurations may be suitably utilized to permit conveying of materials great distances, up extended heights and around corners.

Utilized in conjunction with the conveyor belt 10 and drive source 16 is a control mechanism or assembly 22 including electrical sensors or probes 24 and 26 fixedly positioned adjacent the lower surface of the upper track 18 of the belt, however, other probe locations to transmit and receive signals may be utilized. The probes are located adjacent opposite edges of the belt 10 defining a line generally perpendicular to the direction of belt travel and are adapted to monitor its movement and feed electrical signals to the control system 22. The control system 22 in turn is adapted to act in a servo-loop configuration, through appropriate circuitry to control electrical current to the motor 16. In this manner, the motive force to the belt may be terminated in response to detection of a rip as indicated by a breakage of any antenna 28 fixedly mounted within the belt for movement therewith.

In the preferred mode, a plurality of antennae are located at fixed, spaced intervals along the belt. These antennae generally are spaced at fifty to one hundred feet apart, more or less, spacing generally being a function of the belt size, speed, degree of rip detection protection desired and the control system 22 being utilized. The antennae are utilized to detect the presence of broken or unbroken belt segments moving past probes 24 an 26. A more complete understanding of a typical probe and control system can be had by reference to the aforementioned patent to Snyder.

Figure 3:
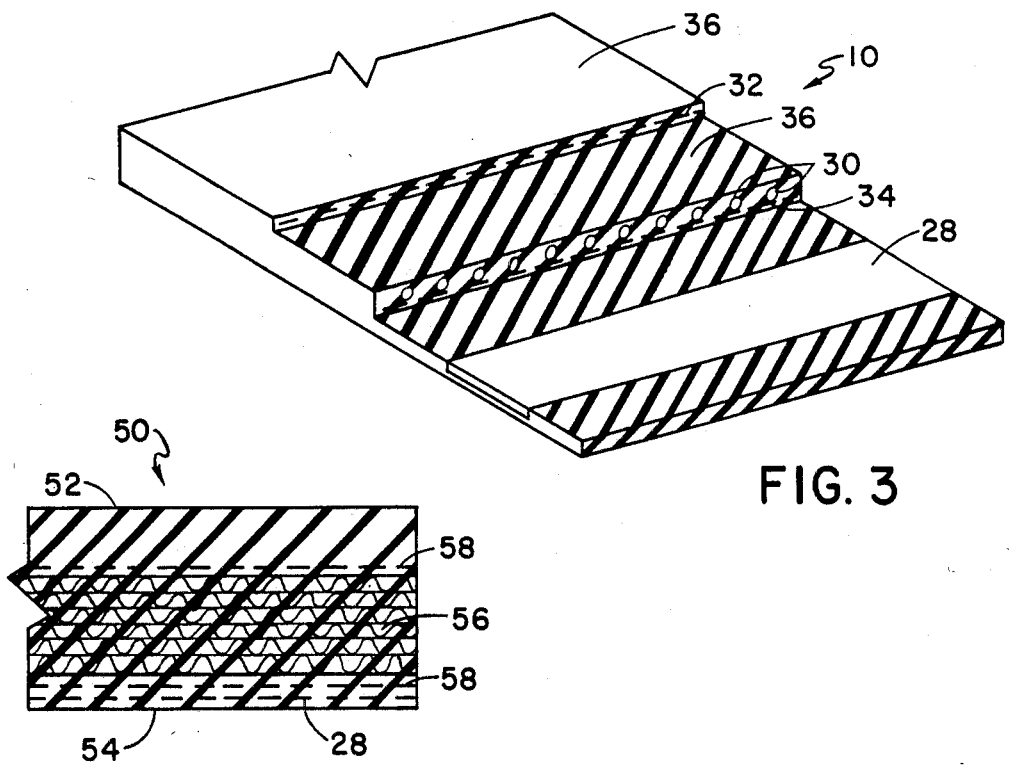
FIG. 3 is a perspective view of the belt of FIGS. 1 and 2 with layers removed to show internal constructions, including the antenna.

Referring to the drawings, FIG. 3 depicts a preferred belt construction including an antennae made in accordance with the instant invention. The preferred antenna is shown in a conveyor belt wherein it may be beneficially utilized. The belt 10, as shown particularly in FIG. 3, may include steel cables 30 which assist in preventing the belt from stretching in a direction of belt movement and which provide greater strength to the belt. Reinforcement in both the length and width of the belt is provided by fabric sheets or breakers 32 and 34 on opposite sides of the centrally located cables 30. Layers 36 of vulcanized elastomeric material such as rubber, natural or synthetic, or combinations thereof blended for belting purposes, are located on opposite sides of the cables 30 and sheets 32 and 34. The cables 30, sheets 32, 34 and layers 36 all are present in continuous loop configuration for carrying out a conveying function.

Figure 4:
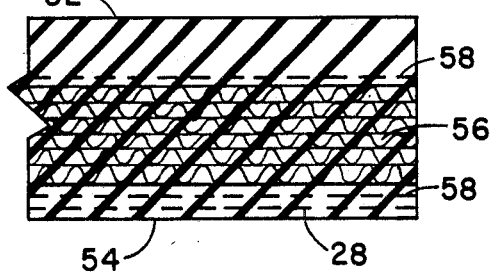
FIG. 4 is a sectional view of an alternate belt assembly employing antennae of the instant invention.

Referring to the drawings, an alternate preferred belt construction employing the antennae of the instant invention is shown in FIG. 4. The belt 50 has rubber upper and lower cover layers 52 and 54 on opposite faces. Rubberized fabric or carcass layers 56 are located between the cover layers with fabric sheets or breakers 58 being located at interfaces between the rubberized fabric layers and cover layers. The breakers are constructed of a fabric material and function to aid in bonding the carcass layers 56 to the cover layers 52, 54 as well as adding impact resistance to the belt. The antennae 28 are located within the cover layer 54. The breakers 58, covers 52, 54 and fabric carcass 56 extend continuously along the length of the endless belt. The antennae are spaced along the length of the belt and are configured to carry electrical changes in the form of signals from a transmitter probe 24 to a receiver probe 26 for rip detection purposes. It should be understood, however, that the antennae 10, 50 of the instant invention can function equally well in a belt assembly with or without cables 30. Breaker plies 58 are preferably utilized in a location between the antennae and steel cables, if steel cables are employed.

Each antenna 28 is fabricated of rubber compound mixed using conventional rubber mixing equipment. The rubber preferably contains a majority of natural or synthetic rubber in appropriate blends to constitute a majority of the composition. This majority may constitute from about 50% to 70% by weight of each composite antenna. Preferably, the rubber component should be between 58% and 63% by weight in the preferred embodiment. Particularly it is preferred that the rubber be one of natural rubber, styrene butadiene rubber (SBR), cis-polybutadiene, neoprene, Hydrin ®, rubber chlorinated polyethylene, nitrile rubbers, silicon rubbers, chlorosulfonated polybutadiene, and mixtures thereof.

The second most prevalent component of the composite material of each antenna should be electrically conductive carbon black. A preferred carbon black is presently marketed by Akzo Chemie Nederland B.V., a Dutch company, and sold under the trade name of "Ketjen EC". The properties of this material are discussed in the September-October 1977 issue of Rubber Chemistry and Technology published by the Rubber Division, American Chemical Society, Inc. It is not sufficient in the practice of the instant invention that the carbon black be electrically conducting as that term is generally understood; the carbon black must be substantially electrically conductive such as Ketjen EC.

Ketjen EC has a lower bulk density, i.e. a lower weight per unit volume, than typical reinforcing carbon blacks commercially available today. Ketjen EC has a specific gravity of about 2.05 plus or minus about 2% as compared to typical carbon blacks which have a specific gravity of from about 1.82 to about 1.86 plus or minus about 2%.

The carbon black employed in the practice of the invention constitutes from about 10% to about 30% by weight of the composite antenna, and preferably from 20% to about 30%. Increased carbon loading is possible, but produces little in the way of enhanced conductivity and risks decreased antennae durability due to lower rubber content. The remaining chemicals and additives of the antenna material include well known antioxidant agents, life extenders, wear resistant materials, vulcanization promoters, processing aids and the like and constitute between about 0% and 40% and preferably about 12% to about 26% by weight, of the antenna material.

The constitutent components of the antenna material are preferably mixed in well-known manner and calendared to an appropriate, even thickness. The calendared material can then be cut to desired shape and size to fit across the belt extending from edge to edge for carrying electrical signals thereacross. During fabrication, the constitutent interior portions of the belt are laid up or plied together prior to vulcanization. The electrically conductive rubber antennae are then spaced along the length of the belt in a sandwich between the bottom cover layer and the composite interior belt structure portions and then vulcanized in the usual, well known manner.

During the process of vulcanization of the belt laminate, the elastomeric rubber surrounds each antenna, coadheres with the rubber of each antennae to adheringly position each antenna in the belt at a proper spacing. The vulcanized rubber provides an excellent bond to forestall slippage of the antennae within the belt during conveyor operation. This non-slipping condition is desirable since antenna slippage towards either belt edge or along the linear path of belt travel during conveyor operation could cause a malfunction of the detection function.

Each antenna is preferably about eight (8) to ten (10) inches in width and extends substantially fully across the transverse dimension of the belt or at least a distance extending from a position opposing one probe to a position opposing the other probe and sufficient to protect portions of the belt where ripping is likely to occur. Each antenna is normally between 0.030 and 0.060 inches in thickness and preferably about 0.032 inches in thickness and constitutes about 10% or less of the total belt thickness. The probes are generally about four (4) to six (6) inches in length measured in a direction perpendicular to belt travel and of a width of about eight (8) to ten (10) inches, substantially equal to that of the antennae, measured in the direction of belt travel. Variations in these dimensions and rations are acceptable.

When employed with lower covers of about ¼ inch in thickness or greater, the antennas become fully incorporated into the belt during vulcanization and the belt assumes an even thickness along its length. If, however, thinner lower covers are employed, as for example, covers of about 1/16 inch or less, the antennas will be fixedly positioned in the belt but, the belt will have a greater thickness at the antenna locations than at other locations. The rip detecting capabilities of a system employing such a belt will not, however, be lost. Further, the greater thickness of the belt at the locations of the antennas will not normally detract from the mechanical operation of such belts.

Belts resulting from the instant invention are possessed of antennae having an electrical resistance across the antennae of not more than the equivalent of 6000 ohms and preferably less than the equivalent of 3000 ohms when proportionated to the resistance across a 5.5"×0.5" plug of vulcanized antenna material 0.075" in thickness, resistance of the plug being determined along the 5.5" dimension.

EXAMPLE I

Four unvulcanized rubber blends were made in accordance with Table I using conventional rubber mixing techniques.

TABLE I

| Blend # | (parts by weight) | | | |
|---|---|---|---|---|
| | 1 | 2 | 3 | 4 |
| Natural Rubber | 50.00 | 45.00 | 40.00 | 30.00 |
| Cis-polybutadien ASTM 101 HA Oil | 34.37 | 34.37 | 34.37 | 34.37 |
| Styrenebutadiene ASTM 101 HA Oil | 34.37 | 34.37 | 34.37 | 34.37 |
| HYDRIN ® -400[1] | — | 5.00 | 10.00 | 20.00 |
| Gum Rosin | 2.00 | 2.00 | 2.00 | 2.00 |
| Paratertiary-octyl phenol-formaldehyde | 2.00 | 2.00 | 2.00 | 2.00 |
| Stearic Acid | 1.50 | 1.50 | 1.50 | 1.50 |
| ZnO | 3.00 | 3.00 | 3.00 | 3.00 |
| Dimethyl-butyl-phenyl-Phenylenediamine | 4.00 | 4.00 | 4.00 | 4.00 |
| Paraffin | 1.00 | 1.00 | 1.00 | 1.00 |
| Trimethyl-dihydro-quinoline | 5.00 | 5.00 | 5.00 | 5.00 |
| | 137.24 | 137.24 | 137.24 | 137.24 |

[1]Trademark of The B. F. Goodrich Company

Each of the rubber blends was then combined with selected carbon blacks, sulfur and accelerators, formed into a 5.5"×0.5" plug 0.75" in thickness under vulcanization conditions and tested for electrical resistance across the plug, the results being set forth in Tables II-V. All entries are parts by weight unless otherwise noted.

TABLE II

| Square # | 11 | 12 | 13 | 14 | 15 | 16 | 17 | 18 | 19 |
|---|---|---|---|---|---|---|---|---|---|
| Blend #1 | 137.24 | 137.24 | 137.24 | 137.24 | 137.24 | 137.24 | 137.24 | 137.24 | 137.24 |
| Furnace carbon black (HAF HS) | 10.00 | 20.00 | 30.00 | | | | | | |
| Vulcan C low conductive carbon black | | | | 10.00 | 20.00 | 30.00 | | | |
| Ketjen EC carbon black | | | | | | | 10.00 | 20.00 | 30.00 |
| Sulfur | 0.60 | 0.60 | 0.60 | 0.60 | 0.60 | 0.60 | 0.60 | 0.60 | 0.60 |
| Sulfenamide accelerators | 2.25 | 2.25 | 2.25 | 2.25 | 2.25 | 2.25 | 2.25 | 2.25 | 2.25 |
| Electrical resistance, ohms | * | * | * | * | * | * | * | 25000 | 300 |

* = greater than 20 megohms

TABLE III

| Square # | 21 | 22 | 23 | 24 | 25 | 26 | 27 | 28 | 29 |
|---|---|---|---|---|---|---|---|---|---|
| Blend #2 | 137.24 | 137.24 | 137.24 | 137.24 | 137.24 | 137.24 | 137.24 | 137.24 | 137.24 |
| Furnace carbon black (HAF HS) | 10.00 | 20.00 | 30.00 | | | | | | |
| Vulcan C low conductive carbon black | | | | 10.00 | 20.00 | 30.00 | | | |
| Ketjen EC carbon black | | | | | | | 10.00 | 20.00 | 30.00 |
| Sulfur | 0.60 | 0.60 | 0.60 | 0.60 | 0.60 | 0.60 | 0.60 | 0.60 | 0.60 |
| Sulfenamide accelerators | 2.25 | 2.25 | 2.25 | 2.25 | 2.25 | 2.25 | 2.25 | 2.25 | 2.25 |
| Electrical | * | * | * | * | * | * | * | 6000 | 360 |

TABLE III-continued

| Square # | 21 | 22 | 23 | 24 | 25 | 26 | 27 | 28 | 29 |
|---|---|---|---|---|---|---|---|---|---|
| resistance, ohms | | | | | | | | | |

* = greater than 20 megohms

TABLE IV

| Square # | 31 | 32 | 33 | 34 | 35 | 36 | 37 | 38 | 39 |
|---|---|---|---|---|---|---|---|---|---|
| Blend #3 | 137.24 | 137.24 | 137.24 | 137.24 | 137.24 | 137.24 | 137.24 | 137.24 | 137.24 |
| Furnace carbon black (HAF HS) | 10.00 | 20.00 | 30.00 | | | | | | |
| Vulcan C low conductive carbon black | | | | 10.00 | 20.00 | 30.00 | | | |
| Ketjen EC carbon black | | | | | | | 10.00 | 20.00 | 30.00 |
| Sulfur | 0.60 | 0.60 | 0.60 | 0.60 | 0.60 | 0.60 | 0.60 | 0.60 | 0.60 |
| Sulfenamide accelerators | 2.25 | 2.25 | 2.25 | 2.25 | 2.25 | 2.25 | 2.25 | 2.25 | 2.25 |
| Electrical resistance, ohms | * | * | * | * | * | * | * | 12000 | 300 |

* = greater than 20 megohms

TABLE V

| Square # | 41 | 42 | 43 | 44 | 45 | 46 | 47 | 48 | 49 |
|---|---|---|---|---|---|---|---|---|---|
| Blend #4 | 137.24 | 137.24 | 137.24 | 137.24 | 137.24 | 137.24 | 137.24 | 137.24 | 137.24 |
| Furnace carbon black (HAF HS) | 10.00 | 20.00 | 30.00 | | | | | | |
| Vulcan C low conductive carbon black | | | | 10.00 | 20.00 | 30.00 | | | |
| Ketjen EC carbon black | | | | | | | 10.00 | 20.00 | 30.00 |
| Sulfur | 0.60 | 0.60 | 0.60 | 0.60 | 0.60 | 0.60 | 0.60 | 0.60 | 0.60 |
| Sulfenamide accelerators | 2.25 | 2.25 | 2.25 | 2.25 | 2.25 | 2.25 | 2.25 | 2.25 | 2.25 |
| Electrical resistance, ohms | * | * | * | * | * | * | * | 3000 | 270 |

* = greater than 20 megohms

While the instant invention is described above with regard to a preferred embodiment, it is intended to be covered broadly within the spirit and scope of the appended claims.

What is claimed is:

1. A system for detecting a rip in a vulcanized rubber containing conveyor belt moveable in a closed path of travel comprising sensor probe means positioned along the path of travel, and a belt having electrically conductive antennae vulcanized into the belt for carrying signals transversely across the belt during normal belt operating conditions and for ceasing the carrying of signals when the belt and antenna are ripped, said antennae being formed from a vulcanizable material principally comprising rubber and also comprising substantially electrically conductive particles of carbon black, the carbon black being between about 10% to less than about 30% by weight and the rubber between about 50% and about 70% by weight of the material of the antenna.

2. The system as set forth in claim 1 wherein said electrically conductive carbon black constitutes between 20% and 30% by weight of the antenna.

3. The system as set forth in claim 2 wherein the carbon black has a specific gravity of about 2.05 plus or minus 2%.

4. For use in a conveyor belt rip detection system, a plurality of electrically conductive means, each extending transversely across a vulcanized conveyor belt substantially from edge to edge, periodically spaced along the direction of movement of the belt, said means including a blend of vulcanizable rubber and substantially electrically conductive carbon black which constitutes in excess of 10% but less than about 30% by weight of the blend, the antenna being vulcanized into the belt.

5. A vulcanized conveyor belt moveable in a closed path of travel, pairs of sensor probes positioned along the path of travel, a probe in each pair aligned with opposing edges of the belt defining a line generally perpendicular to the direction of belt motion, said belt including electrically conductive antennae transversing the belt in a direction perpendicular to the direction of motion, periodically spaced along the belt for carrying signals across the belt from probe to probe during normal conditions and for ceasing the carrying of signals when the belt and an antenna is ripped, said antennae being constructed of a vulcanizable material principally comprising rubber and also comprising substantially electrically conductive carbon black of a specific gravity of 2.05 plus or minus 2% and constituting between about 10% and 30% by weight of the material of th antennae, the antennae being vulcanized into the structure of the belt.

* * * * *